US011854671B2

(12) United States Patent
Rong et al.

(10) Patent No.: US 11,854,671 B2
(45) Date of Patent: Dec. 26, 2023

(54) METHOD AND APPARATUS FOR IDENTIFYING HETEROGENEOUS GRAPH AND PROPERTY OF MOLECULAR SPACE STRUCTURE AND COMPUTER DEVICE

(71) Applicant: TENCENT TECHNOLOGY (SHENZHEN) COMPANY LIMITED, Guangdong (CN)

(72) Inventors: Yu Rong, Shenzhen (CN); Yu He, Shenzhen (CN); Junzhou Huang, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 641 days.

(21) Appl. No.: 17/078,369

(22) Filed: Oct. 23, 2020

(65) Prior Publication Data
US 2021/0043283 A1   Feb. 11, 2021

Related U.S. Application Data

(63) Continuation of application No. PCT/CN2019/113947, filed on Oct. 29, 2019.

(30) Foreign Application Priority Data

Oct. 30, 2018 (CN) .......................... 201811278487.4

(51) Int. Cl.
*G16C 20/70* (2019.01)
*G06F 16/901* (2019.01)
(Continued)

(52) U.S. Cl.
CPC ......... *G16C 20/70* (2019.02); *G06F 16/9024* (2019.01); *G06F 18/24* (2023.01); *G16C 20/80* (2019.02); *G16C 20/90* (2019.02)

(58) Field of Classification Search
CPC ........ G16C 20/70; G16C 20/80; G16C 20/90; G16C 20/30; G06F 16/9024; G06F 18/24;
(Continued)

(56) References Cited

U.S. PATENT DOCUMENTS 9,326,698 B2 * 5/2016 Blanco ................. A61B 5/4094
11,521,712 B2 * 12/2022 Fan .......................... G06N 5/046
(Continued)

FOREIGN PATENT DOCUMENTS

CN   103399951 A   11/2013
CN   107341499 A   11/2017
(Continued)

OTHER PUBLICATIONS

Olayan et al., DDR: efficient computational method to predict drug-target interactions using graph mining and machine learning approaches, Bioinformatics, 2017 (Year: 2017).*
(Continued)

*Primary Examiner* — Mohammad K Islam
(74) *Attorney, Agent, or Firm* — Sughrue Mion, PLLC

(57) ABSTRACT

A method and an apparatus for identifying a heterogeneous graph and a property corresponding to a molecular space structure and a computer device are provided. The method includes: characterizing a topology structure included in a heterogeneous graph to generate feature information; generating feature vectors corresponding to key nodes on the topology structure included in the heterogeneous graph according to sampling information obtained by sampling the heterogeneous graph and the feature information; aggregating the feature vectors to generate a graph representation vector corresponding to the heterogeneous graph; and classifying the heterogeneous graph according to the graph representation vector to obtain a classification prediction result of the heterogeneous graph.

18 Claims, 7 Drawing Sheets

(51) Int. Cl.
*G16C 20/80* (2019.01)
*G16C 20/90* (2019.01)
*G06F 18/24* (2023.01)

(58) Field of Classification Search
CPC .... G06F 18/2411; G06N 3/042; G06N 3/045; G06V 10/245
See application file for complete search history.

(56) References Cited

U.S. PATENT DOCUMENTS

| | | | |
|---|---|---|---|
| 2018/0246913 A1 | | 8/2018 | Huang et al. |
| 2018/0341754 A1* | | 11/2018 | Fan ........................ G06N 5/046 |
| 2019/0095806 A1* | | 3/2019 | Martinez Canedo .. G06N 20/00 |

FOREIGN PATENT DOCUMENTS

| | | |
|---|---|---|
| CN | 107506617 A | 12/2017 |
| CN | 110263780 A | 9/2019 |

OTHER PUBLICATIONS

Wang et al. ,Drug repositioning by integrating target information through a heterogeneous network model, 2014, Bioinformatics (Year: 2014).*

Meng et al. ,Iteratively collective prediction of disease-gene associations through the incomplete network, 2017, IEEE (Year: 2017).*

Qu et al. , SNMDA: A novel method for predicting microRNA-disease associations based on sparse neighbourhood, 2018, Wiley) (Year: 2018).*

Chen et al. ,HGIMDA: Heterogeneous graph inference for miRNA-disease association prediction, 2016 (Year: 2016).*

Peng et al. , HNMDA: heterogeneous network-based miRNA-disease association prediction, 2018, Molecular Genetics and Genomics (Year: 2018).*

Translation of Written Opinion of the International Searching Authority dated Feb. 1, 2020 in International Application No. PCT/CN2019/113947.

Extended European Search Report dated Dec. 9, 2021 in European Application No. 19877767.4.

Hamilton et al., "Representation Learning on Graphs: Methods and Applications", IEEE Data Engineering Bulletin, Apr. 10, 2018, pp. 1-24 (24 pages total).

Persona et al., "Information-Theoretic Indices Usage for the Prediction and Calculation of Octanol—Water Partition Coefficient", Acta Poloniae Pharmaceutica—Drug Research, vol. 64, No. 4, 2007, pp. 311-317 (7 pages total).

Yang, "Disease, Drug, and Target Association Predictions by Integrating Multiple Heterogeneous Sources", Master of Science Thesis, Department of Electrical Engineering and Computer Science, Case Western Reserve University, Aug. 27, 2021, pp. 1-62 (70 pages total).

International Search Report of PCT/CN2019/113947 dated Feb. 1, 2020 [PCT/ISA/210].

Written Opinion of PCT/CN2019/113947 dated Feb. 1, 2020 [PCT/ISA/237].

* cited by examiner

METHOD AND APPARATUS FOR IDENTIFYING HETEROGENEOUS GRAPH AND PROPERTY OF MOLECULAR SPACE STRUCTURE AND COMPUTER DEVICE

CROSS-REFERENCE TO RELATED APPLICATION(S)

This application is a bypass continuation application of International Application No. PCT/CN2019/113947 filed on Oct. 29, 2019, which claims priority to Chinese Patent Application No. 201811278487.4, entitled "METHOD AND APPARATUS FOR IDENTIFYING HETEROGENEOUS GRAPH AND PROPERTY OF MOLECULAR SPACE STRUCTURE AND DEVICE" and filed with the Chinese Patent Office on Oct. 30, 2018, the disclosures of which are herein incorporated by reference in their entireties.

FIELD

The disclosure relates to the field of computer technologies, and in particular, to a method and an apparatus for identifying a heterogeneous graph and a property corresponding to a molecular space structure and a computer device.

BACKGROUND

Various types of identification based on machine learning have been important tools for researching and analyzing various types of source data in various application scenarios. For example, in application scenarios such as image processing and natural language processing, based on machine learning, large-scale classification and identification of source data may be implemented, so as to rapidly obtain a classification prediction result related to the source data and accelerate the implementation of functions in the application scenarios.

As a classic implementation architecture of machine learning, a neural network has achieved great success in the field of classification and identification. A plurality of models and architectures based on neural networks may be used for solving classification problems in machine learning. Generally, source data inputted to the neural network has one thing in common, that is, is grid data. That is, a neural network is used for specially processing data of a similar grid structure. In the related art, some data of a non-grid structure, for example, a heterogeneous graph, is rarely processed by using a neural network.

SUMMARY

Embodiments of the disclosure provide a method for identifying a heterogeneous graph and even a property corresponding to a molecular space structure by using a neural network, that is, a method and an apparatus for identifying a heterogeneous graph and a property corresponding to a molecular space structure, and a computer device.

According to an aspect of an example embodiment, a method for identifying a heterogeneous graph, performed by computing device, is provided. The method includes:

characterizing a topology structure included in a heterogeneous graph (or a topology structure of a heterogeneous graph) to generate feature information;

generating feature vectors corresponding to key nodes on the topology structure according to sampling information obtained by sampling the heterogeneous graph and the feature information;

aggregating the feature vectors to generate a graph representation vector corresponding to the heterogeneous graph; and classifying the heterogeneous graph according to the graph representation vector to obtain a classification prediction result of the heterogeneous graph.

According to an aspect of an example embodiment, a method for identifying a property corresponding to a molecular space structure, performed by computing device, is provided. The method includes:

obtaining a heterogeneous graph of a molecular space structure, the molecular space structure including a chemical molecular structure and a protein molecular structure;

characterizing a molecular structure included in the heterogeneous graph to generate feature information;

generating feature vectors corresponding to key nodes on a topology structure included in the heterogeneous graph according to sampling information obtained by sampling the heterogeneous graph and the feature information;

aggregating the feature vectors to generate a graph representation vector corresponding to the heterogeneous graph; and classifying the heterogeneous graph according to the graph representation vector to obtain a classification prediction result indicating a property corresponding to the molecular space structure corresponding to the heterogeneous graph.

According to an aspect of an example embodiment, an apparatus for identifying a heterogeneous graph is provided. The apparatus includes:

at least one memory configured to store program code; and at least one processor configured to read the program code and operate as instructed by the program code, the program code including:

feature description code configured to cause at least one of the at least one processor to characterize a topology structure included in a heterogeneous graph (or a topology structure of a heterogeneous graph) to generate feature information;

vector construction code configured to cause at least one of the at least one processor to generate feature vectors corresponding to key nodes on the topology structure according to sampling information obtained by sampling the heterogeneous graph and the feature information;

aggregation code configured to cause at least one of the at least one processor to aggregate the feature vectors to generate a graph representation vector corresponding to the heterogeneous graph; and classification code configured to cause at least one of the at least one processor to classify the heterogeneous graph according to the graph representation vector to obtain a classification prediction result of the heterogeneous graph.

According to an aspect of an example embodiment, an apparatus for identifying a property corresponding to a molecular space structure is provided. The apparatus includes:

at least one memory configured to store program code; and at least one processor configured to read the program code and operate as instructed by the program code, the program code including:

molecular structure obtaining code configured to cause at least one of the at least one processor to obtain a heterogeneous graph of a molecular space structure, the molecular space structure including a chemical molecular structure and a protein molecular structure;

molecular structure description code configured to cause at least one of the at least one processor to characterize a molecular structure included in the heterogeneous graph to generate feature information;

molecular feature extraction code configured to cause at least one of the at least one processor to generate feature vectors corresponding to key nodes on a topology structure included in the heterogeneous graph according to sampling information obtained by sampling the heterogeneous graph and the feature information;

structure vector representation code configured to cause at least one of the at least one processor to aggregate the feature vectors to generate a graph representation vector corresponding to the heterogeneous graph; and property classification code configured to cause at least one of the at least one processor to classify the heterogeneous graph according to the graph representation vector to obtain a classification prediction result indicating a property corresponding to the molecular space structure corresponding to the heterogeneous graph.

According to an aspect of an example embodiment, a computer device is provided. The computer device includes at least one processor, and at least one memory storing computer-readable instructions, the computer-readable instructions, when executed by the at least one processor, implementing the foregoing method.

According to an aspect of an example embodiment, a non-transitory computer-readable storage medium is provided. The storage medium stores computer-readable instructions, the computer-readable instructions, when executed by at least one processor, implementing the foregoing method.

BRIEF DESCRIPTION OF THE DRAWINGS

To describe the technical solutions in the embodiments of the disclosure more clearly, the following briefly describes the accompanying drawings required for describing the embodiments of the disclosure.

DETAILED DESCRIPTION

To make the objectives, technical solutions, and advantages of the disclosure clearer, the following further describes the disclosure in detail with reference to the accompanying drawings and the embodiments. It is to be understood that the specific implementations described herein are merely used to explain the disclosure but are not intended to limit the protection scope of the disclosure. When the following descriptions are made with reference to the accompanying drawings, unless indicated otherwise, same numbers in different accompanying drawings represent same or similar elements.

Pharmaceutical analysis is the science of studying the quality of drugs and control patterns of the drugs. In the pharmaceutical analysis, it is a very important task to determine, according to the structure of a compound (a small-molecule compound or generally any of various compounds in some parts herein) or protein, some chemical and/or biological properties such as the toxicity, solubility, carcinogenicity, and the like of the compound or protein. In the related art, it is challenging to implement or perform the task by using a neural network. The structure (molecular space structure) of a compound or protein is not a grid structure. A graph obtained by graphically representing the structure is a heterogeneous graph. It has a great significance in the field of pharmaceutical analysis to construct a generalized neural network structure based on graph data of the heterogeneous graph to identify and classify the molecular space structure of the compound to further identify and classify the compound or protein and improve the efficiency and accuracy of identification and classification.

In the embodiments of the disclosure, a task of determining the chemical or biological property of a compound or protein in the pharmaceutical analysis is modeled as a classification problem in machine learning, and processing that adapts to the neural network is performed for identifying the heterogeneous graph, to construct a vector representation that may be identified by the neural network to achieve a rapid identification of the heterogeneous graph, especially the molecular space structure. Specifically, the structural formula of a compound may be transformed into a vector in Euclidean space based on representation learning, and the vector is then classified by using a machine learning algorithm to determine the chemical or biological property of the compound.

Figure 1:
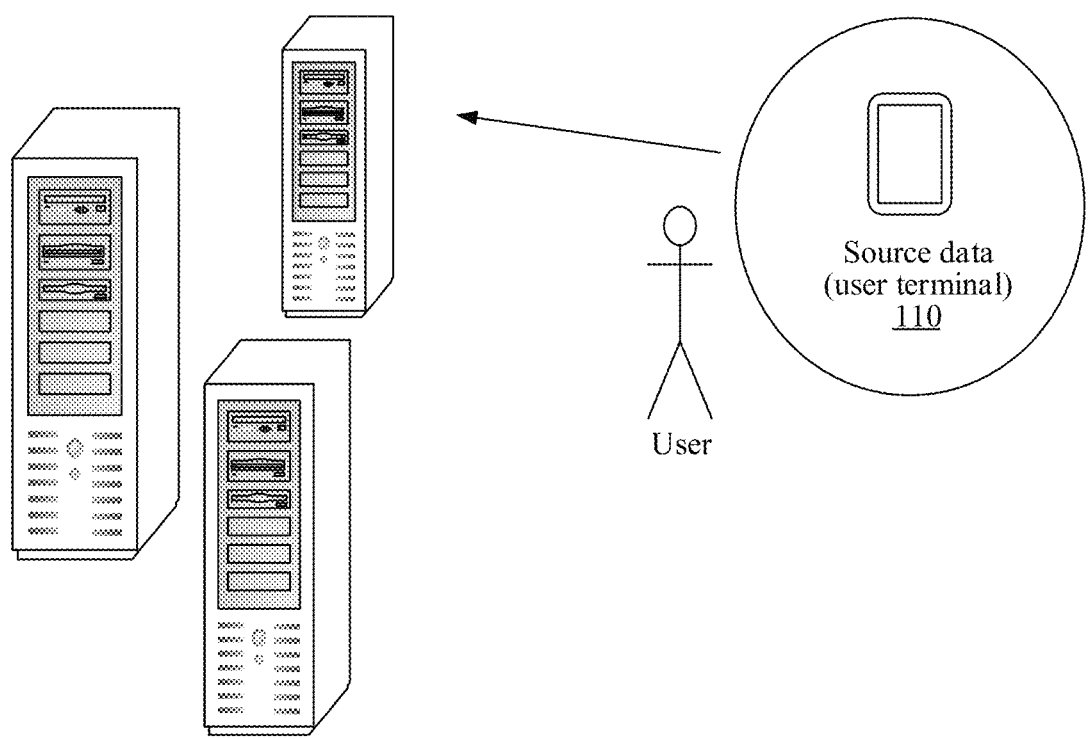
FIG. 1 is a schematic diagram of an implementation environment according to the disclosure.

FIG. 1 is a schematic diagram of an implementation environment according to the disclosure. In an example embodiment, the implementation environment includes a data source 110 and a computing platform 130. The data source 110 requests source data identified by the computing platform 130. The source data includes grid data and graph data corresponding to a heterogeneous graph, and does not have a grid structure.

The computing platform 130 uses a method provided by the disclosure to process the graph data corresponding to the heterogeneous graph to obtain a graph representation vector corresponding to the heterogeneous graph with a non-grid structure and eventually obtain a classification prediction result.

For the grid data, the computing platform 130 merely needs to directly perform classification and identification by using an existing neural network, for example, a convolutional neural network, and additional processing in the example embodiment of the disclosure does not need to be performed.

The data source 110 may be a user terminal held by a user. According to an embodiment of the disclosure, the heterogeneous graph that needs to be classified and predicted is obtained by using a heterogeneous graph identification operation requested by the user terminal, thereby identifying properties of a corresponding chemical substance, a protein substance or the like.

With the cooperation of the data source 110 and the computing platform 130, the heterogeneous graph is classified and identified. It is to be understood that a specific framework of the implementation environment depends on a specific application scenario. In different scenarios, there are other architectural deployments in addition to the deployments of the data source 110 and the computing platform 130 in the implementation environment.

For example, in an application scenario that provides services for heterogeneous graph identification required by applications, service interfaces are configured on the computing platform 130 is performed. Correspondingly, the applications that require heterogeneous graph identification merely need to invoke the service interfaces to implement the heterogeneous graph identification.

In addition, there are further various application scenarios such as heterogeneous graph identification in a social network and heterogeneous graph identification in a sensor network. Examples are not listed herein one by one.

It is to be understood that the descriptions of the implementation environment is only the description of one implementation environment, but is not limited thereto. For a given heterogeneous graph, the inputted heterogeneous graph may be classified and predicted by using a method for identifying a heterogeneous graph according to the disclosure.

Figure 2:
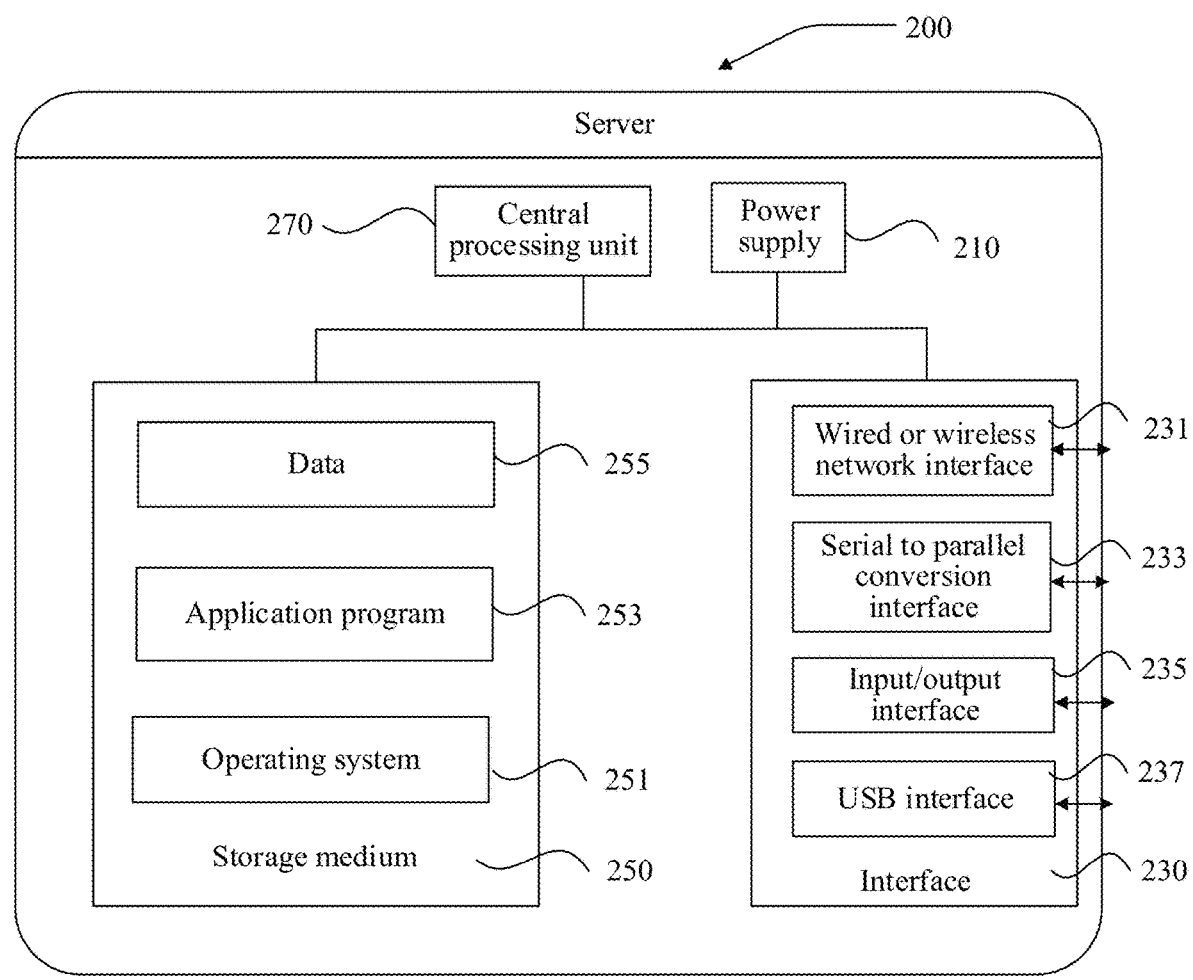
FIG. 2 is a structural block diagram of the hardware of a server according to an embodiment of the disclosure.

FIG. 2 is a structural block diagram of the hardware of a server 200 according to an embodiment of the disclosure. The server 200 is merely an example for description of the disclosure, and should not be considered as limiting. It also should not be understood that the server 200 is necessarily required to include one or more components of the example server 200 shown in FIG. 2.

The computing platform 130 of the implementation environment shown in FIG. 1 is implemented by the deployment of the server 200 in an example embodiment.

The hardware structure of the server 200 may vary greatly because of differences in configuration or performance. As shown in FIG. 2, the server 200 includes a power supply 210, an interface 230, at least one storage medium 250, and at least one central processing unit (CPU) 270.

The power supply 210 is configured to provide a working voltage for hardware devices on the server 200.

The interface 230 includes at least one of a wired or wireless network interface 231, a serial to parallel conversion interface 233, an input/output interface 235, and a USB interface 237, which is configured to communicate with external devices.

The storage medium 250, serving as a carrier of resource storage, may be a random storage medium, a magnetic disk, an optical disc or the like. Resources stored thereon include an operating system 251, an application program 253, data 255, and the like. A storage manner may be transient storage or permanent storage. The operating system 251 is configured to manage and control various hardware devices on the server 200 and the application program 253 to implement the computation and processing of the massive data 255 by the CPU 270. The operating system may be Windows Server™, Mac OS X™, Unix™, Linux™, FreeBSD™ or the like. The application program 253 is a computer program that completes at least one specific work based on the operating system 251, and may include at least one module (not shown in FIG. 2). Each module may include a series of operation instructions for the server 200. The data 255 may be photos, pictures, and the like stored in the disk.

The CPU 270 may include one or more processors, may be arranged to communicate with the storage medium 250 by using a bus, and may be configured to operate and process the massive data 255 in the storage medium 250.

As described in detail above, the server 200 may read the forms of a series of operation instructions stored in the storage medium 250 by using the CPU 270 to identify the heterogeneous graph.

Figure 3:
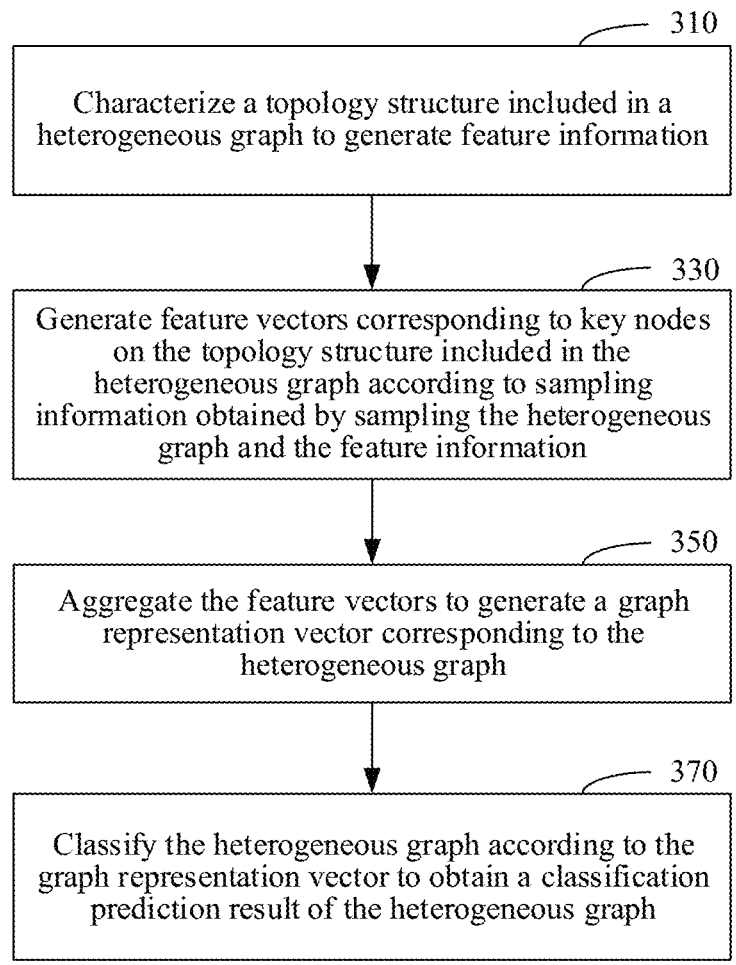
FIG. 3 is a flowchart of a method for identifying a heterogeneous graph according to an embodiment of the disclosure.

FIG. 3 is a flowchart of a method for identifying a heterogeneous graph according to an embodiment of the disclosure. In an example embodiment, the method for identifying a heterogeneous graph, as shown in FIG. 3, includes at least the following operations 310, 330, 350, 370:

Operation 310. Characterize a topology structure included in a heterogeneous graph to generate feature information.

The heterogeneous graph is a graphical description of nodes on a topology structure and relationships between the nodes. The topology structure is constructed by the nodes and the relationships between the nodes. For example, a graphical representation of a heterogeneous information network is the heterogeneous graph, and the topology structure included in the heterogeneous graph corresponds to a network topology of the heterogeneous information network in space.

For example, for the heterogeneous information network such as a sensor network, interaction between existing sensor nodes constitute the corresponding network topology in space. The topology structure obtained for the network topology by graphically describing the sensor network is used for forming the heterogeneous graph.

As described above, data used in the heterogeneous graph that graphically describes the nodes and the relationships between the nodes is not a grid structure. Therefore, the heterogeneous graph cannot be used as an input to extract a convolutional feature in the neural network.

However, to identify a heterogeneous graph, feature information needs to be generated for the heterogeneous graph to facilitate subsequent operations.

The feature information is generated for the topology structure of the heterogeneous graph. The heterogeneous graph is the graphical representation of the heterogeneous information network and is based on a mapping of the network topology in the heterogeneous information network. Therefore, the topology structure in the heterogeneous graph is an important feature of the heterogeneous graph.

The topology structure included in the heterogeneous graph is used to generate the feature information.

The generated feature information is a definition of the heterogeneous graph and also feature description information of the heterogeneous graph. Therefore, the heterogeneous graph is described based on the generated feature information to obtain neural network input data that may accurately describe the topology structure in the heterogeneous graph and seek the implementation of classifying and predicting non-grid structure data by using the neural network.

The generated feature information describes the stored nodes on the one hand, and describes the relationships between the nodes on the other hand. Therefore, in an example embodiment, the feature information includes node feature vectors and relationship feature vectors in the heterogeneous graph. All the node feature vectors form a node feature matrix, and the node feature matrix records feature vectors of all the nodes on the heterogeneous graph. All the relationship feature vectors form a relationship feature matrix corresponding to the nodes, and the relationship feature matrix records feature vectors of all the relationships related to the nodes. The nodes mentioned are the nodes on the topology structure, and may also be referred to as "vertices". The relationships mentioned may be alternatively embodied by edges that connect the nodes.

In an example embodiment, a heterogeneous graph includes relationships between node-type nodes and edge-type nodes to form an included topology structure. Therefore, a process of defining the heterogeneous graph and generating feature information includes:

characterizing nodes on the topology structure included in the heterogeneous graph and relationships between the nodes according to the topology structure to generate the feature information, the feature information including node feature vectors and relationship feature vectors corresponding to the heterogeneous graph.

For the topology structure included in the heterogeneous graph, a node type mapping and an edge type mapping are performed to record all node information and all edge information. The edge information is recorded by an adjacency matrix A, and the scale of the adjacency matrix A is $\mathbb{R}^{K \times N \times N}$. The adjacency matrix A records all the edge information of an edge type in the heterogeneous graph G, where K represents the type of an edge, for example, different chemical bonds in a compound, N represents the quantity of the nodes, and each matrix N×N represents an adjacency matrix including an edge of a type.

Decomposition is performed in the following manner. The nodes and edges may have respective feature vectors, that is, a node feature vector x, the scale of which is $\mathbb{R}^{1 \times C}$, where C represents the quantity of node features, and a relationship feature vector, which is also referred to as an edge feature vector e, the scale of which is $\mathbb{R}^{1 \times L}$, where L represents the quantity of edge features. In a convolutional neural network, a quantity of features is equivalent to a quantity of channels are. The concept of the quantity of features is used in an input layer, and the concept of the quantity of channels is used in a convolutional layer.

For the given heterogeneous graph G(V,E,τ,κ), a node type mapping is τ:V→T, an edge type mapping is κ:E→K, N is the quantity of the nodes, T is a node type set, and K is an edge type set. Through the edge type mapping, the adjacency matrix representing the edge information is converted into a $K^{th}$-order tensor. E is the relationship feature matrix, and is also referred to as an edge feature matrix, the scale of which is $\mathbb{R}^{N \times N \times L}$, where N represents the quantity of the nodes, and L represents the quantity of feature dimensions of the edges. $E_i$ is used for recording the feature vectors of all the edges related to a node i. V is the node feature matrix that records the feature vectors of all the nodes, and the scale is $\mathbb{R}^{N \times C}$.

Through the foregoing definition and description, the characterization of the given heterogeneous graph is implemented, the feature information including the node feature vectors and the relationship feature vectors is obtained, and the network topology is implemented for the heterogeneous information network. That is, while a spatial structure is described, identifying the neural network is also possible.

For example, a molecular space structure corresponding to a compound or protein substance is a heterogeneous information network. Molecules distributed in space and various groups and atoms in the molecules may be used as nodes in the heterogeneous information network. Chemical bonds existing between the nodes are relationships between the nodes. Therefore, chemical formulas or protein structures may be described by using the heterogeneous graph.

Figure 4:
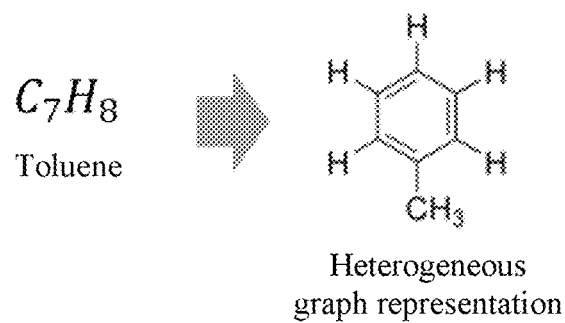
FIG. 4 shows a representation of a heterogeneous graph of a compound according to an embodiment of the disclosure.

FIG. 4 shows a representation of a heterogeneous graph of a compound according to an example embodiment. In the representation of a compound, an atom may be represented by a node V, and a corresponding chemical bond may be represented by an edge E. E also refers to a feature vector. The atoms may be atoms of different elements, for example, hydrogen atoms, and oxygen atoms. A set of elements may be defined as a node type set T.

Similarly, there are various types of the chemical bonds, for example, single bonds, and double bonds. A set of the types of the chemical bonds is defined as an edge type set K. Further, different atoms have different properties, for example, electron quantities, and valence states. As a result, the chemical bonds have different properties. Therefore, descriptions are respectively provided by using the constructed node feature vectors and edge feature vectors. In this manner, the feature information in the heterogeneous graph is generated.

In another example embodiment, before operation 310, the method for identifying a heterogeneous graph further includes:

obtaining a heterogeneous graph corresponding to a heterogeneous information network, the heterogeneous graph being a graphical representation of the heterogeneous information network, the heterogeneous information network including nodes of interest and relationships between the nodes.

The disclosure may implement a neural network-based identification for any heterogeneous graph. That is, for the obtained heterogeneous graph that needs identification, the identification may be completed through the implementation of the disclosure. The heterogeneous graph may be arbitrarily obtained and is not limited to a specific source. Any heterogeneous graph may be implemented through example embodiments of the disclosure. The heterogeneous graph may further include the heterogeneous graph obtained for the heterogeneous information network.

In an example embodiment, a heterogeneous information network is an abstraction of a real world, and forms a topology structure for objects of interest and interactions between the objects. The objects of interest are nodes. The interactions between the objects indicate relationships that exist between the objects. For example, the heterogeneous information network may be a social network, a sensor network, a financial risk control network or the like. Therefore, the disclosure may be widely applied to different types of heterogeneous information networks, thereby implementing classification and analysis, which have very high flexibility and versatility.

Operation 330. Generate feature vectors corresponding to key nodes on the topology structure included in the heterogeneous graph according to sampling information obtained by sampling the heterogeneous graph and the feature information.

After the feature information corresponding to the heterogeneous graph is obtained through the execution of operation 310, the heterogeneous graph may be sampled to obtain a receptive field with a convolution structure corresponding to the key nodes, and the feature vectors corresponding to the key nodes may then be obtained from the feature information by convolving the receptive field.

The sampling of the heterogeneous graph outputs graph topology information based on sampling according to the heterogeneous graph, and obtains the key nodes according to the graph topology information to facilitate the generation of the receptive field for each key node. The receptive field has the convolution structure, which may be used for implementing the extraction of the feature vectors corresponding to the key nodes.

Optionally, the heterogeneous graph sampling may be implemented by using a plurality of sampling methods such as a centrality sampling, a random walk sampling, and a heuristic sampling of the nodes. A new graph corresponding to the heterogeneous graph is outputted based on sampling. The new graph is a graphical representation of the graph topology information of the heterogeneous graph, and the new graph maintains topology information in the heterogeneous graph. The most representative nodes are selected from the nodes included in the heterogeneous graph based on sampling and are used as the key nodes to construct the new graph.

The heterogeneous graph is sampled to select the key nodes. Based on this, the receptive field corresponding to the key nodes is generated. In the neural network, the feature vectors of the key nodes may be extracted from the feature information by using the receptive field corresponding to the key nodes. That is, the generation of the feature vectors corresponding to the key nodes on the topology structure included in the heterogeneous graph is implemented in the manner.

Through the execution of operation 330, the identification of the heterogeneous graph may be performed in the neural network such as the convolutional neural network, and is no longer excluded by the neural network due to the lack of a grid structure.

It is to be understood that, through operation 330, an input layer in the neural network architecture, and a feature extraction layer extracted by the feature vectors may be implemented. The graph topology information outputted by sampling the heterogeneous graph is used as input information of the input layer in the neural network architecture. After the receptive field that may adapt to the feature extraction layer is generated through the graph topology information, the graph topology information is transmitted to the feature extraction layer. The feature vectors are extracted from the feature information by using the receptive field in the feature extraction layer, so as to implement a feature extraction in the neural network architecture, to continue to aggregate a graph representation vector corresponding to the heterogeneous graph in the neural network architecture to perform classification and prediction of the neural network.

Operation 350. Aggregate the feature vectors to generate a graph representation vector corresponding to the heterogeneous graph.

As mentioned above, through the execution of operation 330, the feature vector corresponding to each key node is obtained. Therefore, an aggregation layer in the neural network architecture is introduced into the identification of the heterogeneous graph, thereby implementing the convolutional neural network that may identify the heterogeneous graph. The aggregation layer implemented for this objective is equivalent to a fully connected layer in the existing convolutional neural network, and is used for synthesizing all inputted data. This is similar to the aggregation implemented for the feature vectors in operation 350 of the disclosure.

Each key node has a corresponding feature vector. All the key nodes are included in the topology structure of the heterogeneous graph, which is an initial source of the key nodes. Certainly, the key nodes also exist in the graph topology information. However, the key nodes and the relationships between the key nodes represent the topology structure included in the heterogeneous graph. The topology structure is the main content of the heterogeneous graph. Therefore, the feature vectors corresponding to the whole heterogeneous graph are obtained by aggregating the feature vectors of all the key nodes, that is, the graph representation vector corresponding to the heterogeneous graph is generated.

The generated graph representation vector numerically characterizes the heterogeneous graph. Therefore, the graph representation vector accurately represents the heterogeneous graph and the topology structure included in the heterogeneous graph, and the generated graph representation vector may be applied to the classification and prediction in the process of identifying the heterogeneous graph.

For the calculation of the graph representation vector, more possible aggregation methods may be used, and are not limited to the foregoing aggregation implementation. For example, a max-pooling implementation may also be used.

Operation 370. Classify the heterogeneous graph according to the graph representation vector to obtain a classification prediction result of the heterogeneous graph.

By performing the foregoing operation, the graph representation vector that may numerically characterize the heterogeneous graph is obtained. Therefore, the classification of the heterogeneous graph may be performed in the neural network by using the graph representation vector to obtain an attribute tag belonging to the heterogeneous graph.

Therefore, for a plurality of heterogeneous information networks, especially chemical substances or protein substances that form the heterogeneous information network by the molecular space structure, corresponding properties or attributes may be identified by using the disclosure. That is, the properties or attributes are outputted by using results obtained by the classification and prediction without manual intervention and tedious analysis, which may be inaccurate. An automatic identification is implemented for a plurality of fields related to the heterogeneous information network.

Through the foregoing example embodiments described above, the classification and identification of the heterogeneous graph are implemented, and the efficient and accurate analysis of the corresponding heterogeneous information network of the heterogeneous graph is implemented for the heterogeneous graph. Additionally, according to the disclosure, machine devices may replace manual labor to perform rapid analysis on a large quantity of unknown heterogeneous information networks, for example, unknown compounds. Therefore, the speeds of research and analysis are greatly increased.

Through the foregoing example embodiments described above, data processing of machine learning is no longer limited to grid data, more general graph data, that is, graph data that is more ubiquitous than grid data may be classified and identified, and the performance of the machine learning is enhanced, thereby implementing the extension of a conventional neural network, to implemented an extended neural network.

Figure 5:
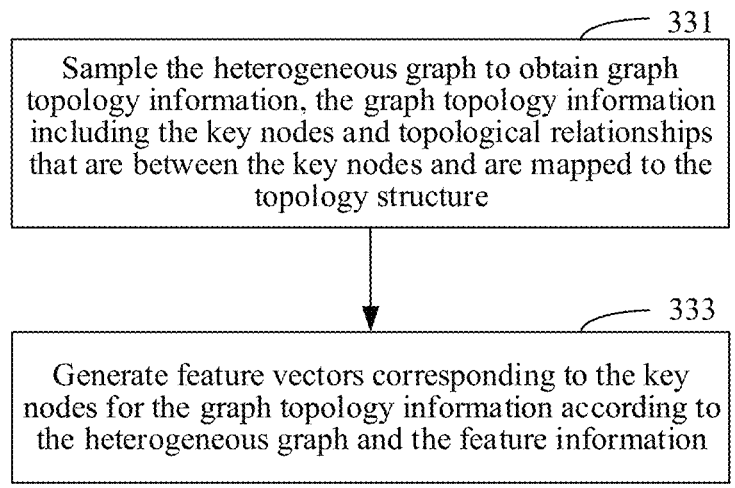
FIG. 5 is a flowchart for describing operation 330 according to the embodiment corresponding to FIG. 3.

FIG. 5 is a flowchart for describing operation 330 according to the embodiment corresponding to FIG. 3. In an example embodiment, as shown in FIG. 5, operation 330 at least includes the following operations 331 and 333:

Operation 331. Sample the heterogeneous graph to obtain graph topology information, the graph topology information including the key nodes and topological relationships that are between the key nodes and are mapped to the topology structure.

As described in the foregoing descriptions, the key nodes are selected from the topology structure included in the heterogeneous graph by sampling the heterogeneous graph, and relationships between corresponding nodes on the topology structure included in the heterogeneous graph are then obtained according to the key nodes, so that original topology information is kept. The topological relationships that may be mapped to the topology structure are reconstructed for the key nodes to obtain the graph topology information.

That is, in another example embodiment, operation 331 includes: performing a node sampling on the topology structure included in the heterogeneous graph, and obtaining the graph topology information according to the sampling information of the node.

The node sampling includes a centrality sampling. Certainly, the node sampling is not limited thereto, and further includes a random walk sampling and/or a heuristic sampling. In the node sampling method that adapts to a setting, the corresponding sampling information is obtained for each node on the topology structure included in the heterogeneous graph, and the key nodes are then selected from the nodes on the topology structure according to the sampling information to obtain the graph topology information.

Operation 333. Generate feature vectors corresponding to the key nodes for the graph topology information according to the heterogeneous graph and the feature information.

For each key node in the graph topology information, the corresponding feature vectors may be generated for the graph topology information according to the heterogeneous graph and the feature information obtained by defining the heterogeneous graph. The generated feature vectors are used for numerically characterizing the corresponding key nodes.

Through the example embodiment, for the heterogeneous graph, that is, the graph data, processing that adapts to the machine learning is performed to obtain input information, that is, the graph topology information, of an input layer of a neural network. The neural network used for processing the graph data is abstracted into operations in two neural network, that is, an operation of sampling the given heterogeneous graph to obtain the graph topology information and an operation of generating the feature vectors according to the feature information, the heterogeneous graph, and the graph topology information, thereby performing final classification prediction.

Figure 6:
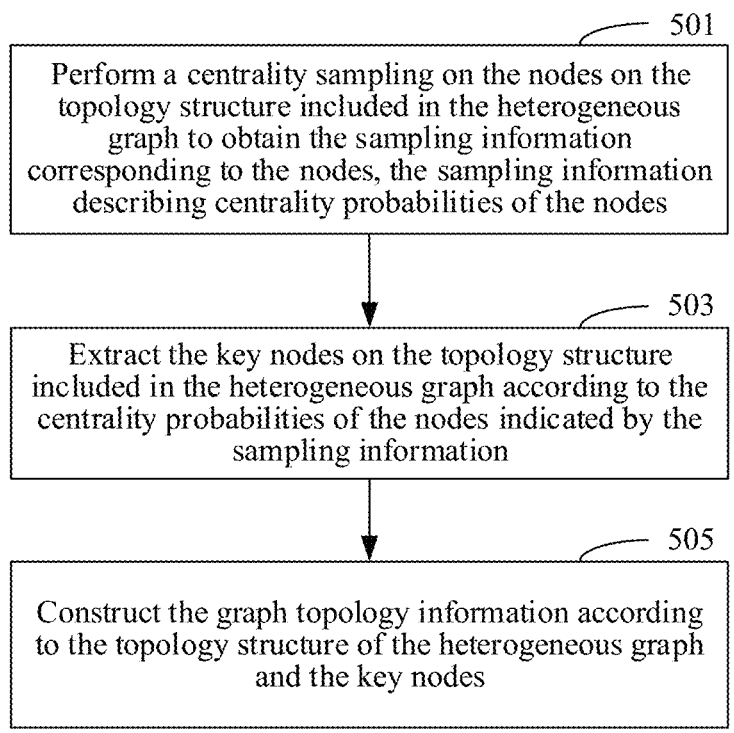
FIG. 6 is a flowchart for describing an operation of performing a node sampling on a topology structure included in a heterogeneous graph and obtaining graph topology information according to sampling information of nodes according to an embodiment of the disclosure.

FIG. 6 is a flowchart for describing an operation of performing a node sampling on a topology structure included in a heterogeneous graph and obtaining graph topology information according to sampling information of nodes according to an embodiment of the disclosure. In an example embodiment, as shown in FIG. 6, the performing a node sampling on a topology structure included in a heterogeneous graph and obtaining graph topology information according to sampling information of nodes at least includes the following operations 501, 503, 505:

Operation 501. Perform a centrality sampling on the nodes on the topology structure included in the heterogeneous graph to obtain the sampling information corresponding to the nodes, the sampling information indicating centrality probabilities of the nodes.

The centrality sampling is performed on each node on the topology structure. The centrality sampling is performed on the each node on the topology structure to obtain the sampling information corresponding to the node. Through the corresponding sampling information, a degree of centrality of the node on the topology structure may be known.

In the graph theory, the centrality of the node represents the importance of the node in the graph. Therefore, a key node may be sampled from the topology structure according to the centrality of the each node. The centrality of the node may be described and measured by using the sampling information obtained by sampling.

The centrality of the node has a plurality of representation methods. For example, the quantity of neighbors of the node is used for representing the centrality of the node. A node with more neighbors has a higher degree of centrality and has a higher probability of becoming a key node.

Correspondingly, the centrality sampling performed on the node is a process of sampling the quantity of neighbors of the node. Therefore, the obtained sampling information includes the quantity of neighbors corresponding to the node. The quantity of neighbors indicates the centrality probability of the node. When the quantity of neighbors is larger, the corresponding centrality probability is higher.

Figure 7:
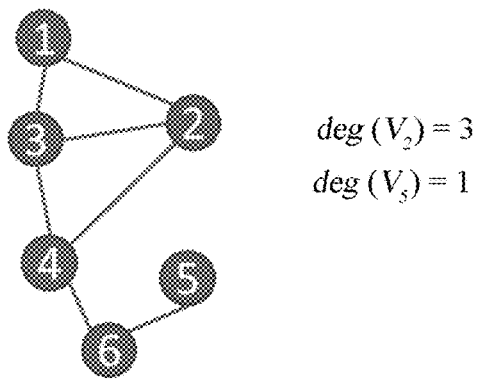
FIG. 7 is a schematic diagram of key nodes in a new graph corresponding to graph topology information and relationships between the key nodes according to an embodiment of the disclosure.

For example, FIG. 7 is a schematic diagram of key nodes in a new graph corresponding to graph topology information and relationships between the key nodes according to an embodiment of the disclosure. As shown in FIG. 7, a degree $\deg(V_2)$ of the node $V_2$ is the quantity of neighbors, and the value is 3. While the value of a degree $\deg(V_5)$ of the node $V_5$ is 1. In this case, the node $V_2$ has a higher probability of being selected as the key node, because the centrality probability corresponding to the node $V_2$ is greater than the centrality probability of the node $V_5$.

Operation 503. Extract the key nodes on the topology structure included in the heterogeneous graph according to the centrality probabilities of the nodes indicated by the sampling information.

As described in operation 501, the key nodes are selected from the nodes on the topology structure according to the centrality probability of the corresponding nodes indicated by the sampling information. That is, a plurality of nodes with a high centrality probability are selected as the key nodes.

Operation 505. Construct the graph topology information according to the topology structure of the heterogeneous graph and the key nodes.

The graph topology information includes the key nodes and the relationships between the key nodes, and the relationships between the key nodes may be mapped to the topology structure of the heterogeneous graph. The obtained relationships between the key nodes in the graph topology information match the topology structure included in the heterogeneous graph.

Therefore, the graph topology information may be constructed according to the topology structure on the heterogeneous graph and the key nodes. Corresponding to the heterogeneous graph, the graph topology information further has corresponding graph data to obtain the new graph extracted based on the heterogeneous graph.

The graph topology information is a description of the new graph on the data, and the new graph is the graphical representation of the graph topology information.

Through the example embodiment, the centralized sampling is implemented for the graph data, that is, the heterogeneous graph, so that subsequent operation is performed for the key nodes, thereby enhancing the operation speed and identification efficiency and simplifying the operation.

Figure 8:
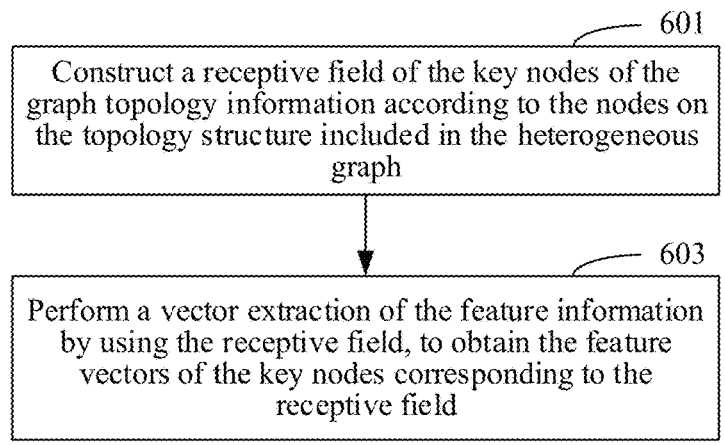
FIG. 8 is a flowchart for describing operation 333 according to the embodiment corresponding to FIG. 5.

FIG. 8 is a flowchart for describing operation 333 according to the embodiment corresponding to FIG. 5. In an example embodiment, as shown in FIG. 8, operation 333 includes at least the following operations 601, 603:

Operation 601. Construct a receptive field of the key nodes of the graph topology information according to the nodes on the topology structure included in the heterogeneous graph.

According to an embodiment of the disclosure, the receptive field is specifically a region mapping of the key nodes (or a mapping region of the key nodes) in the graph topology information to a new graph where the key nodes are located or mapping of the key nodes (or a mapping region of the key nodes) in the graph topology information to a subgraph area where the key nodes are located. For each key node, the corresponding receptive field is generated. The receptive field has a convolution structure, so that a feature vector extraction of the key nodes is implemented.

The receptive field constructed for the key nodes provides the convolution structure for the performed feature vector extraction, so that convolution may be performed, thereby implementing the feature vector extraction of the key nodes.

In an example embodiment, the receptive field is defined as a product of multiplying the receptive field strength by the receptive field weight parameter. As described above, the receptive field is the region mapping of the key nodes on the new graph. Therefore, in comparison with the nodes distributed on the heterogeneous graph, the mapping region is a range of the receptive field. For a node on the heterogeneous graph, in a case that the receptive field strength relative to a key node is 0, it indicates that the node does not fall within the receptive field of the key node.

The receptive field strength of each node relative to the key node is used as an element. The receptive field strength of all the nodes relative to the key node constitutes a matrix of a dimension corresponding to the receptive field strength used to construct the receptive field of the key node.

In addition, the corresponding receptive field weight parameter is a matrix parameter that adapts to the dimension of the receptive field strength. Therefore, an operation for constructing the receptive field is an element multiplication between two matrices.

Therefore, for the key node $\tau$, there are C input channels and K output channels in a layer where the neural network performs the feature vector extraction. A construction of the receptive field $w_{ick}$ related to the node $\tau_i$ in an input channel c and an output channel k may be expressed by using the following formula, that is:

$$w_{ick} = r_i \circ \ldots, \text{ where}$$

"∘" represents a product of elements; $\tau_i$ is a vector of $\mathbb{R}^{N \times 1}$, representing receptive field strength corresponding to other nodes relative to the key node $v_i$; and $\tau$ satisfies:

$\sum_{j=1}^{N} \tau_{ij} = 1$, where $\tau_{ij}$ represents the receptive field strength corresponding to the node $v_j$ relative to the key node $v_i$. For example, for the given key node $v_i$, in a case that $\tau_{ij}=0$, it indicates that the node $v_j$ does not fall within the receptive field of the key node $v_i$.

$h_{ick}$ is a vector of $\mathbb{R}^{N \times 1}$, and is a receptive field weight parameter of the key node $\tau_i$ for all the nodes in the input channel c and the output channel k. The receptive field weight parameter is generated by the topology structure of the heterogeneous graph, and is related to the receptive field strength $\tau_i$.

The foregoing receptive field structure is implemented by a neighborhood structure of the key node. However, in addition, other more construction methods such as a high-order neighbor structure may be used.

Operation 603. Perform a vector extraction of the feature information by using the receptive field, to obtain the feature vectors of the key nodes corresponding to the receptive field.

The feature vector extraction of the key nodes may be performed by using the receptive field constructed for all the key nodes. That is, the feature vector extraction is performed on the presence of the key nodes on the heterogeneous graph by using the receptive field. From the foregoing description, it is to be known that the heterogeneous graph is defined and described by using the feature information. Therefore, the feature vector extraction performed on the key nodes on the heterogeneous graph is performed for the feature information, and it is easier to calculate the feature information that characterizes the heterogeneous graph on data.

Through the example embodiment, the receptive field that may perform the feature vector extraction on the neural network is provided for the graph data, that is, the identification of the heterogeneous graph, thereby effectively avoiding the restriction that the graph data fails to be identified by the neural network under the effect of the receptive field.

Figure 9:
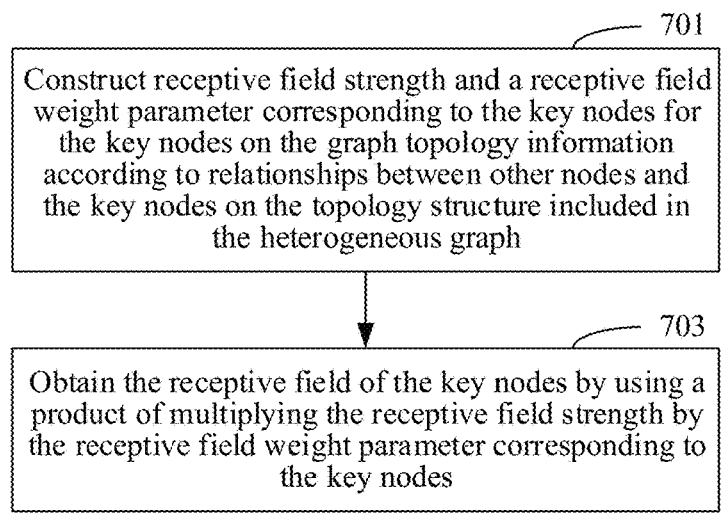
FIG. 9 is a flowchart for describing operation 601 according to the embodiment corresponding to FIG. 8.

FIG. 9 is a flowchart for describing operation 601 according to the embodiment corresponding to FIG. 8. In an example embodiment, as shown in FIG. 9, operation 601 at least includes the following operations:

Operation 701. Construct, with respect to the key nodes on the graph topology information, receptive field strength and a receptive field weight parameter corresponding to the key nodes according to relationships between other nodes and the key nodes on the topology structure included in the heterogeneous graph.

Operation 703. Obtain the receptive field of the key nodes by using a product of multiplying the receptive field strength by the receptive field weight parameter corresponding to the key nodes.

The relationships between the nodes and the key nodes are used for measuring the corresponding receptive field strength, and the receptive field weight parameter is related to the receptive field strength. The relationships between the nodes and the key nodes have different definitions and descriptions according to different construction processes of the receptive field. However, no matter what kind of construction process of the receptive field is used, the relationships between the nodes and the key nodes correspond to the topological relationships on the heterogeneous graph.

For the given key node $v_i$, the receptive field strength $\tau_i$ and the related receptive field weight parameter $h_{ick}$ are constructed according to a neighbor node of the key node $v_i$.

In an implementation of an example embodiment, for the receptive field strength $\tau_i$, if the node $v_j$ is a neighbor node of the key node $v_i$, $$r_{ij} = \frac{1}{|N_{v_i}|},$$

and if not, $\tau_{ij}=0$.

For the implementation of the construction process, the relationships between the nodes and the key nodes are neighbor relationships. The receptive field strength is constructed according to whether the key nodes have neighbor relationships, thereby constructing the related receptive field weight parameter.

For the receptive field weight parameter $h_{ick}$, as described in the foregoing descriptions, the receptive field weight parameter $h_{ick}$ is obtained by the topology structure included in the heterogeneous graph and is related to the receptive field strength $\tau_i$. Specifically, according to the topology structure included in the heterogeneous graph, the receptive field weight parameter is considered according to different edge types on the topology structure.

In an implementation of an example embodiment, the receptive field weight parameter $h_{ick}$ is calculated for edge feature vectors according to relationship feature vectors, and a formula is as follows:

$$h_{ick} = \sum_{\kappa \in K} 1_{[1,L]} \otimes A_\kappa^T(i) \circ E_i W_k(c, k),$$

where $1_{[1,L]}$ represents a vector of $\mathbb{R}^{1 \times L}$; $\otimes$ represents a Kronecker product, and for two given matrices X and y, $$X \otimes Y = \begin{bmatrix} X_{11}Y & \cdots & X_{1n}Y \\ \vdots & \ddots & \vdots \\ X_{m1}Y & \cdots & X_{mn}Y \end{bmatrix}; A_K(i)$$

is a vector of $\mathbb{R}^{1 \times N}$, which is used to represent a related neighbor vector in an adjacency matrix of the key node $v_i$ (an edge type associated with the neighbor is $\kappa$); $E_i$ is a matrix with a scale of $\mathbb{R}^{N \times L}$, representing a relationship feature matrix, which is also referred to as an edge feature matrix.

Through the example embodiment, constructions of the receptive field weight parameter, the receptive field strength, and even the receptive field are implemented to provide the possibility of the classification and identification of non-grid structure data, that is, the heterogeneous graph in the neural network. Under the effect of the constructed receptive field, the classification and identification of the heterogeneous graph may be implemented through the neural network.

In another example embodiment, operation 370 in the method for identifying a heterogeneous graph includes: performing a tag prediction on the graph representation vector by using a trained and optimized loss function to obtain the classification prediction result of the heterogeneous graph relative to given tag data, the classification prediction result being indicated as a tag predicted by the heterogeneous graph.

The loss function is used for a tag corresponding to the given heterogeneous graph in the tag data, the tag indicating information such as properties known by identifying the heterogeneous graph. Specifically, the predicted tag indicates the properties of the heterogeneous information network corresponding to the heterogeneous graph, for example, chemical properties or biological properties of any compound and/or protein substance.

The loss function is obtained by training and optimizing a group of given heterogeneous graphs and corresponding tag data $\{G_i, y_i\}_{i=1}^n$. $G_i$ is the given heterogeneous graph, and $y_i$ represents the tag. The corresponding value indicates properties or attributes of the given heterogeneous graph G.

For example, for the predicted tag $y_i$ of the given heterogeneous graph $G_i$, if the value is 1, it indicates that the compound corresponding to the given heterogeneous graph $G_i$ is toxic. If the value of the tag $y_i$ is 0, it indicates that the compound is not toxic.

In a specific implementation of an example embodiment, the loss function obtained through training and optimization is shown as the following formula:

$$\min_{W_K, W_s, W_t} \frac{1}{n} \sum_{G_t} -y_i \log(p_i) + (1 - y_i)\log(1 - p_i), \text{ where}$$

$p_i = \sigma(x_{G_i})$, $\sigma(x) = 1/(1+e^{-x})$, and n is a quantity of tags, a tag prediction is performed on any graph representation vector by using the weight parameter $W_k$, $W_s$, $W_t$ obtained through learning and training, thereby determining the properties and/or attributes of the heterogeneous graph and even the heterogeneous information network corresponding to the heterogeneous graph through the predicted tag.

Through the foregoing example embodiments described above, various heterogeneous graphs and heterogeneous information networks may be rapidly analyzed based on the machine learning. For the chemical structure of a compound or protein, that is, a heterogeneous information network such as a molecular space structure, and some other heterogeneous information networks, the heterogeneous information network may be constructed by using a data structure such as a graph, and a neural network is constructed for the heterogeneous information network, thereby enhancing the classification performance of the graph, which has great practical significance in various fields.

Through the foregoing example embodiments described above, a representation learning is modeled for the heterogeneous graph through a convolutional neural network model defined on the graph data, thereby providing a universal analysis implementation for different types of heterogeneous graphs.

According to an embodiment of the disclosure, for the given heterogeneous graph, an included topology structure is characterized to generate feature information, and feature vectors corresponding to key nodes on the topology structure included in the heterogeneous graph are then generated through the sampling of the heterogeneous graph and the feature information. Finally, after the feature vectors are aggregated to generate a graph representation vector corresponding to the heterogeneous graph, the heterogeneous graph is classified according to the graph representation vector to obtain a classification prediction result. In the identification of the heterogeneous graph, the feature vectors that may perform a convolutional operation performed in the neural network are obtained through the sampling of the heterogeneous graph and the generation of the feature vectors corresponding to the key nodes. Therefore, the graph representation vector is obtained through the aggregation implemented by using the neural network to obtain the classification prediction result, so that the identification of the heterogeneous graph such as the graphical representation corresponding to the molecular space structure is implemented by using the neural network. Accordingly, the analysis performance related to the heterogeneous graph is effectively improved, the neural network is no longer limited to the classification and identification of network data, and application scenarios are greatly extended.

On the other hand, based on the example embodiments described above, the disclosure further provides a method for identifying a property corresponding to a molecular space structure. The method for identifying a property corresponding to a molecular space structure may be used for identifying a compound and protein substance with unknown properties and learning the properties of the compound and protein substance.

Figure 10:
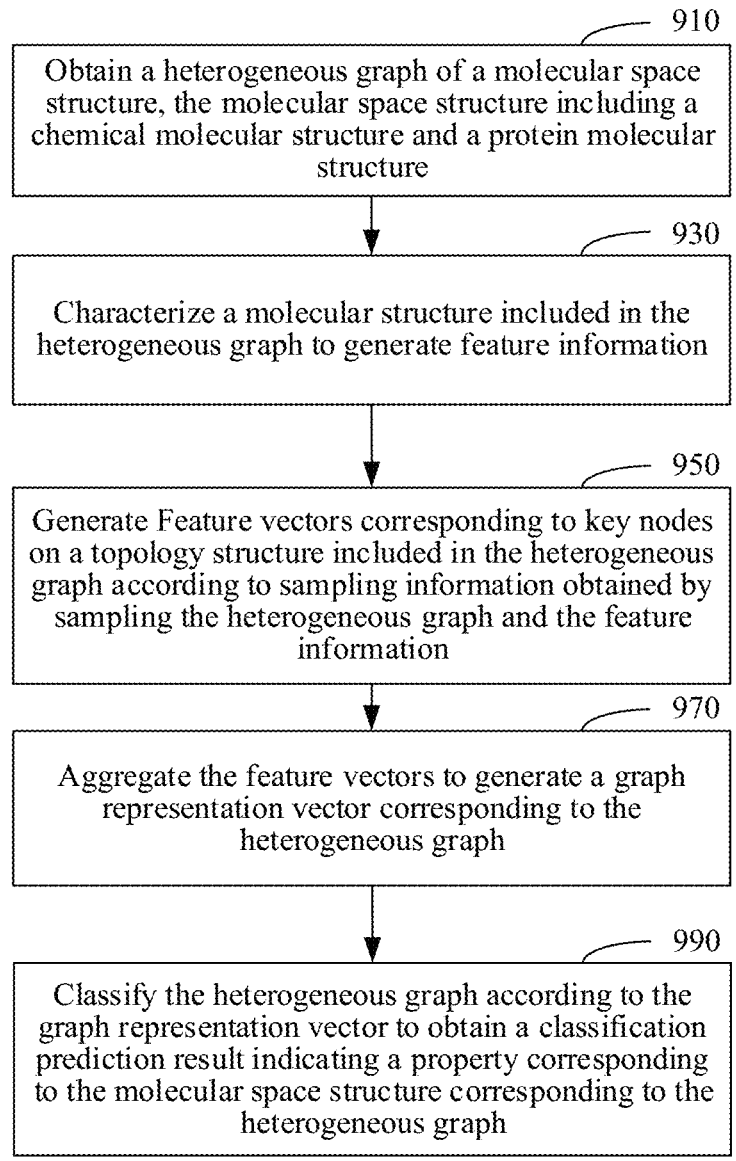
FIG. 10 is a flowchart of a method for identifying a property corresponding to a molecular space structure according to an embodiment of the disclosure.

FIG. 10 is a flowchart of a method for identifying a property corresponding to a molecular space structure according to an example embodiment. In an example embodiment, as shown in FIG. 10, the method for identifying a property corresponding to a molecular space structure at least includes the following operations:

Operation 910. Obtain a heterogeneous graph of a molecular space structure, the molecular space structure including a chemical molecular structure and a protein molecular structure.

Operation 930. Characterize a molecular structure included in the heterogeneous graph to generate feature information.

Operation 950. Generate feature vectors corresponding to key nodes on a topology structure included in the heterogeneous graph according to sampling information obtained by sampling the heterogeneous graph and the feature information.

Operation 970. Aggregate the feature vectors to generate a graph representation vector corresponding to the heterogeneous graph.

Operation 990. Classify the heterogeneous graph according to the graph representation vector to obtain a classification prediction result indicating a property corresponding to the molecular space structure corresponding to the heterogeneous graph.

As described in the foregoing descriptions, the molecular space structure corresponding to the compound and the protein substance is a heterogeneous information network. Molecules distributed in space as well as various groups and atoms in the molecules are nodes distributed on the topology structure of the heterogeneous information network. That is, the molecular structure is the topology structure described above. The molecules as well as the groups and atoms in the molecules included in the compound or the protein substance of which the properties are to be identified are all used as nodes on the topology structure.

Through the implementation of a convolutional neural network defined on the graph data, that is, the data corresponding to the heterogeneous graph, that is, operation 930 to operation 990, the identification of a compound or protein substance corresponding to the non-grid data, that is, the graph data, is implemented based on machine learning.

In another example embodiment, operation 910 includes: obtaining the heterogeneous graph corresponding to the molecular space structure for the molecular space structure including the chemical molecular structure or the protein molecular structure, the heterogeneous graph being a graphical representation of a corresponding chemical substance or protein substance.

For the chemical substance or protein substance that needs to be processed, first, the heterogeneous graph is obtained for the molecular space structure including the chemical molecular structure or the protein molecular structure. Neither the molecular space structure nor the obtained heterogeneous graph is a grid structure. Therefore, an adapting convolutional neural network model needs to be constructed for the graphical representation, that is, the heterogeneous graph of the chemical substance or protein substance, that is, a corresponding embodiment in FIG. 10.

In another example embodiment, operation 990 includes: performing a tag prediction on the graph representation vector by using a loss function to obtain the classification prediction result of the heterogeneous graph relative to tag data. The classification prediction result may indicate properties corresponding to the molecular space structure through a tag of the heterogeneous graph.

The loss function is trained and optimized by using the heterogeneous graph of the given chemical substance or protein substances and the tag data labeled by the heterogeneous graph.

Through the foregoing example embodiments described above, data for the machine learning is no longer limited to grid data, to adapt to a heterogeneous graph of a non-grid structure. A convolutional neural network model is constructed through the implementation of the disclosure, and the identification of the heterogeneous graph is implemented for the constructed convolutional neural network model based on this.

From the perspective of the constructed convolutional neural network model, descriptions are made with reference to the foregoing method implementation.

An original convolutional neural network model includes an input layer, an output layer, and a plurality of hidden layers. There are two types of hidden layers, that is, a convolutional layer and a pooling layer.

The convolutional layer is used for calculating inputted feature information to obtain new feature information by using parameters in the convolutional layer. In particular, it is assumed that the convolutional layer is in an $\iota^{th}$ layer of the convolutional neural network model, the inputted feature information is $X^{(\iota-1)}$, the outputted new feature information is $X^{(\iota)}$, and it is assumed that the inputted feature information $X^{(\iota-1)}$ has $C^{(\iota-1)}$ channels in the $\iota^{th}$ layer, a parameter calculation performed in the convolutional layer may be described in the following convolution formula:

$$x_{ijk}^{(l)} = \sigma\left(\sum_{c \in C^{(l-1)}} X_{ijc}^{(l-1)} * \omega_j^{(l)} + b_k^{(l)}\right), \text{ where}$$

i, j is an index value of the feature information, $x_{ijk}^{(l)}$ represents an output of the feature information indexing i, j on the $k^{th}$ channel, and $\sigma$ is a nonlinear activation function, for example, $\sigma$ may be a rectified linear unit (ReLU), and S is a sigmoid function. The specific form of the function may be: ReLU(x)=max(0, x) and sigmoid $$(x) = \frac{1}{1+e^{-x}}.$$

$X_{ijc}^{(l-1)}$ is a receptive field of the feature information indexing i, j, $\omega_{ijck}^{(l)}$ is a convolution parameter of the feature information indexing i, j for the $\iota^{th}$ layer, the c input channel, and the $k^{th}$ output channel. The dimension of the convolution parameter is the same as the dimension of the $X_{ijc}^{(l-1)}$. For example, if $X_{ijc}^{(l-1)}$ is a 3×3 matrix, and a weight parameter $\omega_{ijck}^{(1)}$ is also a 3×3 matrix. Next, for all the feature information of the index value, the weight parameter $\omega_{ijck}^{(1)}$ is a shared parameter, and $b_k^{(1)}$ is an offset parameter.

The above describes an implementation of the convolutional neural network in the machine learning. However, as described in the foregoing descriptions, the convolutional neural network cannot be used for the identification of the heterogeneous graph. The convolutional neural network follows a default rule that there is a spatial order in a process of sequentially processing the feature information represented by each index, that is, from left to right, and from top to bottom. The spatial order needs to require that convolved data has a grid structure, and the data and the grid structure have invariance and translation equivalence. However, the data graph existing in the heterogeneous graph does not have this characteristic, so that the convolutional neural network cannot be used for a feature extraction.

Therefore, based on an implementation of the disclosure, the convolutional neural network is extended to construct an extended convolutional neural network for the identification of the heterogeneous graph. The extended convolutional neural network is compatible with original input data, that is, grid data.

For the extended convolutional neural network, neural network operations used in the extended convolutional neural network are abstracted into two specific operations, that is:

$G'=\phi(G)$, and $X'=f(X,G,G')$.

As described in the foregoing formulas, for a given inputted graph G (a heterogeneous graph to be identified), the first operation of the extended convolutional neural network is to sample the inputted graph G and generate a sampled new graph G', which is an operation process corresponding to $G'=\phi(G)$; and the second operation is to generate a feature vector X' of a key node according to an inputted feature information matrix X, the given inputted graph G, and the new graph G'. the feature extraction of the graph data performed by the extended convolutional neural network is implemented, and the subsequent identification of the inputted graph G may be completed only by calculations of other layers.

Optionally, it is to be understood that in an implementation of an operation of sampling the given inputted graph G to generate the new graph G', the new graph G' maintains topology information in the inputted graph G. Based on the sampling operation, the most representative node may be selected from a node set V of the inputted graph G to construct the new graph G'.

Optionally, a centrality of the node indicates the importance of the node in the graph, and therefore, a key node V' may be sampled according to the centrality of each node, and then an adjacency matrix A' is reconstructed according to the key node V'. The adjacency matrix A' only stores indexes related to the key node V', N' is the quantity of the key node V' in the new graph, that is |V'|=N'.

The feature vector X corresponding to the key node is generated for the sampled key node set V'. In this process, the receptive field is first generated. After the receptive field $w_{ick}$ is obtained, an outputted feature vector of a key node $v_i$ may be calculated as:

$$x_i' = \sigma\left(\sum_{c\in c}\Omega_{ic}X(c) + W_s x_i\right).$$

In the foregoing formula, $\Omega_{ic}=[w_{ic1}, w_{ic2}, \ldots, w_{icC}]^T$ is a receptive field of the key node $v_i$ on an input channel c, and X(c) is the values of all the inputted feature information on the input channel c.

In this way, to generate a representation vector, that is, the foregoing graph representation vector, for the graph data, a new aggregation layer is introduced, and is similar to a fully connected layer in the convolutional neural network.

Optionally, it is assumed that there is the given inputted graph G and the node set V and the corresponding feature information matrix X, the graph representation vector is:

$$x_G = \sigma\left(\sum_{t\in T} W_t \sum_{v\in V_t} X_v\right).$$

The graph representation vector $x_G$ is obtained by multiplying a feature vector $X_v$ of the key node by a weight parameter $W_t \in \mathbb{R}^{C\times 1}$ corresponding to a node attribute of the key node and then calculating an activation function σ. A weight parameter W is a $\mathbb{R}^{T\times C}$ matrix, and C is the dimension of the feature vector.

A tag prediction of the given inputted graph G in the extended convolutional neural network may be performed by using the obtained graph representation vector.

In the method in the embodiments of the disclosure, a conventional CNN model is extended to process more general graph data. Additionally, an efficient solution for compound and/or protein analysis is provided by combining topology information, node information, and edge information on the heterogeneous graph. The identification of a heterogeneous graph, for example, a graphical representation corresponding to a molecular space structure, may be implemented by using a neural network, so that the analysis performance related to the heterogeneous graph is effectively improved, the neural network is no longer limited to the classification and identification of network data, and application scenarios are greatly extended. The method in the embodiments of the disclosure has flexibility and versatility, and may be widely applied to classification and analysis on different types of heterogeneous networks such as a social network, a sensor network, and a financial risk control network.

The following describes an apparatus embodiment of the disclosure that is used for performing the embodiments of the method for identifying a heterogeneous graph of the disclosure. For details not disclosed in the apparatus embodiment of the disclosure, reference may be made to the embodiments of the method for identifying a heterogeneous graph of the disclosure.

Figure 11:
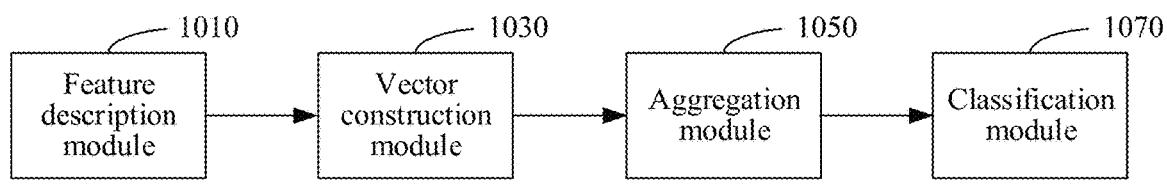
FIG. 11 is a block diagram of an apparatus for identifying a heterogeneous graph according to an embodiment of the disclosure.

FIG. 11 is a block diagram of an apparatus for identifying a heterogeneous graph according to an example embodiment. In an example embodiment, as shown in FIG. 11, the apparatus for identifying a heterogeneous graph includes, but is not limited to, a feature description module 1010, a vector construction module 1030, an aggregation module 1050, and a classification module 1070.

The feature description module 1010 is configured to characterize a topology structure included in a heterogeneous graph to generate feature information.

The vector construction module 1030 is configured to generate feature vectors corresponding to key nodes on a topology structure included in the heterogeneous graph according to sampling information obtained by sampling the heterogeneous graph and the feature information.

The aggregation module 1050 is configured to aggregate the feature vectors to generate a graph representation vector corresponding to the heterogeneous graph.

The classification module 1070 is configured to classify the heterogeneous graph according to the graph representation vector to obtain a classification prediction result of the heterogeneous graph.

In another example embodiment, the feature description module 1010 is further configured to characterize the nodes on the topology structure included in the heterogeneous graph and relationships between the nodes according to the topology structure to generate the feature information, the feature information including node feature vectors and relationship feature vectors corresponding to the heterogeneous graph.

In another example embodiment, the apparatus for identifying a heterogeneous graph further includes a heterogeneous graph obtaining module. The heterogeneous graph obtaining module is configured to obtain a heterogeneous graph corresponding to a heterogeneous information network, the heterogeneous graph being a graphical representation of the heterogeneous information network, the heterogeneous information network including the nodes and the relationships between the nodes.

In another example embodiment, the vector construction module 1070 is configured to:
sample the heterogeneous graph to obtain graph topology information, the graph topology information including the key nodes and topological relationships that are between the key nodes and are mapped to the topology structure; and
generate the feature vectors corresponding to the key nodes for the graph topology information according to the heterogeneous graph and the feature information.

Optionally, the sampling the heterogeneous graph includes: performing a node sampling on the topology structure included in the heterogeneous graph, and obtaining the graph topology information according to the sampling information of the nodes.

Further, in a process that the vector construction module 1070 performs the node sampling on the topology structure included in the heterogeneous graph and obtains the graph topology information according to the sampling information of the node, the vector construction module 1070 is configured to:
perform a centrality sampling on the nodes on the topology structure included in the heterogeneous graph to obtain the sampling information corresponding to the nodes, the sampling information describing centrality probabilities of the nodes;
extract the key nodes on the topology structure included in the heterogeneous graph according to the centrality probabilities of the nodes indicated by the sampling information; and
construct the graph topology information according to the topology structure of the heterogeneous graph and the key nodes.

In another example embodiment, the vector construction module 1030 is configured to:
construct a receptive field of the key nodes of the graph topology information according to the nodes on the topology structure included in the heterogeneous graph; and
perform a vector extraction of the feature information by using the receptive field to obtain the feature vectors of the key nodes corresponding to the receptive field.

In another example embodiment, in a process that the vector construction module 1030 constructs a receptive field of the key nodes of the graph topology information according to the nodes on the topology structure included in the heterogeneous graph,
receptive field strength and a receptive field weight parameter corresponding to the key nodes are constructed for the key nodes on the graph topology information according to relationships between other nodes and the key nodes on the topology structure included in the heterogeneous graph; and
the receptive field of the key nodes is obtained by using a product of multiplying the receptive field strength by the receptive field weight parameter corresponding to the key nodes.

In another example embodiment, the classification module 1070 is configured to:
perform a tag prediction on the graph representation vector by using a trained and optimized loss function to obtain the classification prediction result of the heterogeneous graph relative to given tag data, the classification prediction result being indicated as a tag predicted by the heterogeneous graph.

Figure 12:
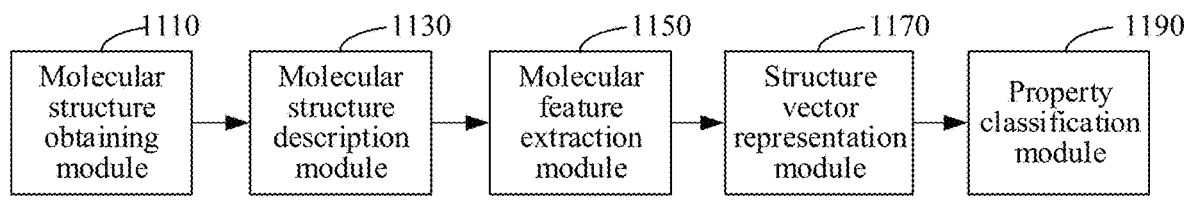
FIG. 12 is a block diagram of an apparatus for identifying a property corresponding to a molecular space structure according to an embodiment of the disclosure.

FIG. 12 is a block diagram of an apparatus for identifying a property corresponding to a molecular space structure according to an example embodiment. In an example embodiment, the apparatus for identifying a property corresponding to a molecular space structure, as shown in FIG. 12, includes, but is not limited to: a molecular structure obtaining module 1110, a molecular structure description module 1130, a molecular feature extraction module 1150, a structure vector representation module 1170, and a property classification module 1190.

The molecular structure obtaining module 1110 is configured to obtain a heterogeneous graph of a molecular space structure, the molecular space structure including a chemical molecular structure and a protein molecular structure.

The molecular structure description module 1130 is configured to characterize a molecular structure included in the heterogeneous graph to generate feature information.

The molecular feature extraction module 1150 is configured to generate feature vectors corresponding to key nodes on a topology structure included in the heterogeneous graph according to sampling information obtained by sampling the heterogeneous graph and the feature information.

The structure vector representation module 1170 is configured to aggregate the feature vectors to generate a graph representation vector corresponding to the heterogeneous graph.

The property classification module 1190 is configured to classify the heterogeneous graph according to the graph representation vector to obtain a classification prediction result indicating a property corresponding to the molecular space structure corresponding to the heterogeneous graph.

In another example embodiment, the molecular structure obtaining module 1110 is configured to:
obtain the heterogeneous graph corresponding to the molecular space structure for the molecular space structure including the chemical molecular structure or the protein molecular structure, the heterogeneous graph being a graphical representation of a corresponding chemical substance or protein substance.

In another example embodiment, the property classification module 1190 is configured to:
perform a tag prediction on the graph representation vector by using a loss function to obtain the classification prediction result of the heterogeneous graph relative to tag data, the classification prediction result indicating the property corresponding to the molecular space structure through a tag of the heterogeneous graph, the loss function being trained and optimized by using a heterogeneous graph of a given chemical substance or protein substance and tag data labeled by the heterogeneous graph.

Optionally, the disclosure further provides a device. The device is, for example, a machine device. The machine device may be applied to the implementation environment in FIG. 1, to perform all or some of the operations in the method shown in any one of FIG. 3, FIG. 5, FIG. 6, FIG. 8, FIG. 9, and FIG. 10. The device includes:

a processor; and a memory, configured to store instructions that may be executed by the processor; where the processor is configured to implement the foregoing method.

A specific implementation of operations performed by the processor of the apparatus in an embodiment is described in detail in the foregoing embodiments, and details are not described herein.

The disclosure may be implemented as a computer-readable code written on a computer-readable recording medium. The computer-readable recording medium may be any type of recording device in which data is stored in a computer-readable manner. Examples of the computer-readable recording medium include a ROM, a RAM, a compact disc (CD)-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Also, functional programs, codes, and code segments for implementing the disclosure can be readily construed by programmers of ordinary skill in the art, to which the disclosure pertains.

At least one of the components, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above example embodiments may be implemented in algorithms that execute on one or more processors. Furthermore, the components, elements or units represented by a block or processing operations may employ any number of related art techniques for electronics configuration, signal processing and/or control, data processing and the like. Software components, modules or units, or code, can be implemented or written using a computer programming language.

While the disclosure has been particularly shown and described with reference to example embodiments thereof, it will be understood that various changes in form and details may be made therein without departing from the spirit and scope of the following claims.

What is claimed is:

1. A method for identifying a heterogeneous graph, performed by computing device, the method comprising:

obtaining a heterogeneous graph of a molecular space structure, the molecular space structure comprising a chemical molecular structure and a protein molecular structure;

characterizing a molecular structure included in the heterogeneous graph to generate feature information;

generating feature vectors corresponding to key nodes on a topology structure according to sampling information obtained by sampling the heterogeneous graph and the feature information;

aggregating the feature vectors to generate a graph representation vector corresponding to the heterogeneous graph; and classifying the heterogeneous graph according to the graph representation vector to obtain a classification prediction result of the heterogeneous graph, wherein the classifying the heterogeneous graph includes:

training and optimizing a neural network, the neural network being a group of given heterogeneous graphs, and performing a tag prediction on the graph representation vector by using the trained and optimized neural network to obtain the classification prediction result of the heterogeneous graph relative to given tag data, the classification prediction result being indicated as a tag predicted by the heterogeneous graph.

2. The method according to claim 1, wherein the characterizing comprises:

characterizing nodes on the topology structure and relationships between the nodes according to the topology structure to generate the feature information, the feature information comprising node feature vectors and relationship feature vectors corresponding to the heterogeneous graph.

3. The method according to claim 1, further comprising:

obtaining the heterogeneous graph, which is a graphical representation of a heterogeneous information network, the heterogeneous information network including the nodes and relationships between the nodes.

4. The method according to claim 1, wherein the generating comprises:

sampling the heterogeneous graph to obtain graph topology information, the graph topology information comprising the key nodes and topological relationships between the key nodes, the topological relationships being mapped to the topology structure; and generating the feature vectors corresponding to the key nodes according to the heterogeneous graph and the feature information.

5. The method according to claim 4, wherein the sampling comprises:

performing a node sampling on the topology structure, and obtaining the graph topology information according to sampling information of the nodes.

6. The method according to claim 5, wherein the performing the node sampling and obtaining the graph topology information comprises:

performing a centrality sampling on the nodes on the topology structure to obtain the sampling information of the nodes, the sampling information of the nodes indicating centrality probabilities of the nodes;

extracting the key nodes on the topology structure according to the centrality probabilities of the nodes indicated by the sampling information of the nodes; and constructing the graph topology information according to the topology structure of the heterogeneous graph and the key nodes.

7. The method according to claim 4, wherein the generating the feature vectors corresponding to the key nodes according to the heterogeneous graph and the feature information comprises:

constructing a receptive field of the key nodes of the graph topology information according to the nodes on the topology structure; and performing a vector extraction of the feature information by using the receptive field to obtain the feature vectors corresponding to the key nodes.

8. The method according to claim 7, wherein the constructing comprises:

with respect to the key nodes on the graph topology information, constructing receptive field strength and a receptive field weight parameter corresponding to the key nodes according to relationships between the key nodes and other nodes on the topology structure; and obtaining the receptive field of the key nodes by using a product of multiplying the receptive field strength by the receptive field weight parameter corresponding to the key nodes.

9. A method for identifying a property corresponding to a molecular space structure, performed by a computing device, the method comprising:

obtaining a heterogeneous graph of a molecular space structure, the molecular space structure comprising a chemical molecular structure and a protein molecular structure;

characterizing a molecular structure included in the heterogeneous graph to generate feature information;

generating feature vectors corresponding to key nodes on a topology structure included in the heterogeneous graph according to sampling information obtained by sampling the heterogeneous graph and the feature information;

aggregating the feature vectors to generate a graph representation vector corresponding to the heterogeneous graph; and classifying the heterogeneous graph according to the graph representation vector to obtain a classification prediction result indicating a property corresponding to the molecular space structure corresponding to the heterogeneous graph, wherein the classifying the heterogeneous graph includes:
training and optimizing a loss function using a heterogeneous graph of a given chemical substance or protein substance and tag data labeled by the heterogeneous graph, and performing a tag prediction on the graph representation vector by using the loss function to obtain the classification prediction result of the heterogeneous graph relative to tag data, the classification prediction result indicating the property corresponding to the molecular space structure through a tag of the heterogeneous graph.

10. The method according to claim 9, wherein the obtaining comprises:

obtaining the heterogeneous graph corresponding to the molecular space structure for the molecular space structure including the chemical molecular structure or the protein molecular structure, the heterogeneous graph being a graphical representation of a corresponding chemical substance or protein substance.

11. An apparatus for identifying a heterogeneous graph, comprising:

at least one memory configured to store program code; and at least one processor configured to read the program code and operate as instructed by the program code, the program code comprising:

obtaining code configured to cause at least one of the at least one processor to obtain a heterogeneous graph of a molecular structure, the molecular space structure comprising a chemical molecular structure and a protein molecular structure;

feature description code configured to cause at least one of the at least one processor to characterize a molecular structure included in the heterogeneous graph to generate feature information;

vector construction code configured to cause at least one of the at least one processor to generate feature vectors corresponding to key nodes on a topology structure according to sampling information obtained by sampling the heterogeneous graph and the feature information;

aggregation code configured to cause at least one of the at least one processor to aggregate the feature vectors to generate a graph representation vector corresponding to the heterogeneous graph; and classification code configured to cause at least one of the at least one processor to classify the heterogeneous graph according to the graph representation vector to obtain a classification prediction result of the heterogeneous graph, wherein the classification code is further configured to cause at least one of the at least one processor to:

train and optimize a neural network, the neural network being a group of given heterogeneous graphs, and perform a tag prediction on the graph representation vector by using the trained and optimized neural network to obtain the classification prediction result of the heterogeneous graph relative to given tag data, the classification prediction result being indicated as a tag predicted by the heterogeneous graph.

12. The apparatus according to claim 11, wherein the feature description code is further configured to cause at least one of the at least one processor to characterize nodes on the topology structure and relationships between the nodes according to the topology structure to generate the feature information, the feature information comprising node feature vectors and relationship feature vectors corresponding to the heterogeneous graph.

13. The apparatus according to claim 11, wherein the program code further comprises:
obtaining code configured to cause at least one of the at least one processor to obtain the heterogeneous graph, which is a graphical representation of a heterogeneous information network, the heterogeneous information network including the nodes and relationships between the nodes.

14. The apparatus according to claim 11, wherein the vector construction code comprises:
sampling sub-code configured to cause at least one of the at least one processor to sample the heterogeneous graph to obtain graph topology information, the graph topology information comprising the key nodes and topological relationships between the key nodes, the topological relationships being mapped to the topology structure; and
generation sub-code configured to cause at least one of the at least one processor to generate the feature vectors corresponding to the key nodes according to the heterogeneous graph and the feature information.

15. The apparatus according to claim 14, wherein the sampling sub-code is configured to cause at least one of the at least one processor to perform a node sampling on the topology structure, and obtaining the graph topology information according to sampling information of the nodes.

16. An apparatus for identifying a property corresponding to a molecular space structure by using the apparatus according to claim 11, the apparatus for identifying the property comprising:
at least one memory configured to store program code;
at least one processor configured to read the program code and operate as instructed by the program code, the program code comprising molecular structure obtaining code configured to cause at least one of the at least one processor to obtain a heterogeneous graph of a molecular space structure, the molecular space structure comprising a chemical molecular structure and a protein molecular structure; and
the apparatus for identifying the heterogeneous graph according to claim 13, wherein the characterized topology structure is a molecular structure included in a heterogeneous graph, and the classification prediction result indicates a property corresponding to the molecular space structure corresponding to the heterogeneous graph.

17. A computer device, comprising:
at least one processor; and
at least one memory storing computer-readable instructions, the computer-readable instructions, when executed by the at least one processor, implementing the method according to claim 1.

18. A non-transitory computer-readable storage medium storing computer-readable instructions, the computer-readable instructions, when executed by at least one processor, implementing the method according to claim 1.

* * * * *